(12) United States Patent
Bhavar et al.

(10) Patent No.: US 12,428,422 B2
(45) Date of Patent: Sep. 30, 2025

(54) PURINE DERIVATIVES AS SIK-3 INHIBITORS

(71) Applicant: RHIZEN PHARMACEUTICALS AG, Basel (CH)

(72) Inventors: Prashant K. Bhavar, Hyderabad (IN); Srikant Viswanadha, Hyderabad (IN); Sridhar Veeraraghavan, Hyderabad (IN); Babu Govindarajulu, Hyderabad (IN); Swaroop Kumar Venkata Satya Vakkalanka, Basel (CH)

(73) Assignee: RHIZEN PHARMACEUTICALS AG, Basel (CH)

( * ) Notice: Subject to any disclaimer, the term of this patent is extended or adjusted under 35 U.S.C. 154(b) by 508 days.

(21) Appl. No.: 17/997,438

(22) PCT Filed: May 11, 2021

(86) PCT No.: PCT/IB2021/054026
§ 371 (c)(1),
(2) Date: Oct. 28, 2022

(87) PCT Pub. No.: WO2021/229452
PCT Pub. Date: Nov. 18, 2021

(65) Prior Publication Data
US 2023/0167116 A1    Jun. 1, 2023

(30) Foreign Application Priority Data
May 14, 2020 (IN) .............................. 202041020320

(51) Int. Cl.
*A61P 35/02* (2006.01)
*A61K 45/06* (2006.01)
*C07D 473/34* (2006.01)

(52) U.S. Cl.
CPC ............ *C07D 473/34* (2013.01); *A61K 45/06* (2013.01); *A61P 35/02* (2018.01)

(58) Field of Classification Search
CPC ................................. A61P 35/02; A61K 45/06
See application file for complete search history.

(56) References Cited

U.S. PATENT DOCUMENTS

| | | |
|---|---|---|
| 2011/0118257 A1 | 5/2011 | Muthuppalaniappan et al. |
| 2012/0289496 A1 | 11/2012 | Nagarathnam et al. |
| 2014/0364447 A1 | 12/2014 | Vakkalanka et al. |

FOREIGN PATENT DOCUMENTS

| | | |
|---|---|---|
| WO | 2011055215 A2 | 5/2011 |
| WO | 2012151525 A1 | 11/2012 |
| WO | 2014195888 A1 | 12/2014 |
| WO | 2018009544 A1 | 1/2018 |
| WO | 2019111185 A1 | 6/2019 |

OTHER PUBLICATIONS

International Search Report issued in PCT/IB2021/054026 on Aug. 6, 2021.

*Primary Examiner* — Yong S. Chong
(74) *Attorney, Agent, or Firm* — Blank Rome LLP

(57) ABSTRACT

The present invention relates to novel inhibitors of salt-inducible kinase-3 (SIK3), methods of preparing them, pharmaceutical compositions containing them and methods for the treatment and/or prevention of kinase mediated diseases or disorders using them.

6 Claims, 6 Drawing Sheets

PURINE DERIVATIVES AS SIK-3 INHIBITORS

This application is the U.S. national phase of International Patent Application No. PCT/IB2021/054026, filed May 11, 2021, which claims the benefit of Indian Patent Application number 202041020320, filed May 14, 2020, the entire contents of which is hereby incorporated by reference.

FIELD OF THE INVENTION

The present invention relates to novel salt-inducible kinase-3 (SIK-3) inhibitors, to methods of preparing them, pharmaceutical compositions containing them and to methods for the treatment, prevention and/or amelioration of SIK-3 mediated diseases or disorders using them.

BACKGROUND OF THE INVENTION

The salt-inducible kinases, generally named as SIKs, are highly evolutionarily conserved serine/threonine protein kinases belonging to a family of AMP-activated protein kinase (AMPK). Overexpression of SIK2 and SIK3 has been observed in many tumors, whereas SIK1 expression was significantly lower in tumors than in normal tissues. SIKs, mainly stimulated by ACTH, LKB1, TGF-β, and autophosphorylation, may play crucial roles in regulating multiple signal pathways in cancer cells and controlling a series of cellular processes including cell proliferation and cell apoptosis. More recent studies about SIKs are emerging, and their overexpression is found in a few specific types of cancers. See Wen-Qi Du et al., *Expert Opin. Ther. Targets* (2015) 20(4):477-485.

Overexpression of SIK3 markedly promotes cell proliferation by upregulating gene expression of cyclinDs and cyclinEs, and also accelerates GUS cell cycle progression. Thus, it lends a survival advantage to cancer cells, as well as being associated with the clinicopathological scenarios of ovarian cancer patients. Evidence has revealed that there are two downstream signalling mediators of SIK3: c-Src and phosphoinositide-3-kinase (PI3K). Id.

SIK3 is the latest understood member of the SIK subfamily that is found rather ubiquitous in a variety of tissues. One study has reported evidence that via liver kinase B1 (LKB1), SIK3 can take part in the phosphorylation of the class IIa histone deacetylases (HDACs), thereby stimulating 14-3-3 binding and nucleocytoplasmic trafficking of class IIa HDACs, which regulates various physiological and pathological cellular programs. SIK3, linked to the activation of c-Src described as a downstream signalling mediator of SIK3 during the promotion of GUS progression via upregulating the gene expression of cyclinDs and cyclinE and simultaneously downregulates the expression of p21Waf/Cip1 and p27Kip protein which bestows survival advantages to cancer cells for growth. In addition, the cSrc-PI3K signalling cascade has also been observed in response to the overexpression of SIK3 in the ovarian cancer cells. Id.

SIK3 has also been reported to be overexpressed in human ovarian cancers. In line with this literature evidence, researchers demonstrated specific upregulation of SIK3 following stimulation with high salt on cancer cell lines. Interestingly, higher expression of SIK3 have been observed in triple negative breast cancer cell lines (MDA-MB-231 and BT-20) which are known to exert treatment resistance. Identification of SIK3 could possibly offer novel therapeutic targets to treat triple negative breast cancers. Importantly, MCF10A cell lines (non-malignant breast epithelial cell line) did not show significant SIK3 expression under high salt treatment conditions, possibly suggesting SIK3 expression requires other cancer-associated gene machinery. See, e.g., Amara et. al., PLoS ONE 12(6): e0180097. https://doi.org/10.1371/journal. pone.0180097.

SIK3 has been reported to be overexpressed in high salt/IL-17 environments and mediate cell proliferation, inflammation and metastasis in MCF-7 breast cancer cells. Through a phage display system from ovarian cancer ascites, researchers have identified SIK3 as a novel epithelial ovarian cancer (EOC)-specific tumor-associated antigen. SIK3 overexpression markedly promoted cell proliferation and enabled cells to grow in mice. Decreased SIK3 expression in SKOV3 cells consistently abolished SKOV3 tumorigenic potency through modulation of the protein levels of cell cycle regulators. Highly expressed cytoplasm-localized SIK3 was detected in approximately 55% of breast cancer samples. Representatively, SIK3 has been regarded as a novel ovarian cancer tumor-associated antigen (TAA) by a screening system with malignant ascitic antibodies in a phage library. See, e.g., Wen-Qi Du et al., supra.

Recently, the SIKs were also shown to be critical targets inhibited by the oncoprotein GNAS through PKA-mediated phosphorylation. GNAS is mutationally activated in a subset of pancreatic adenocarcinomas, and suppression of the activity of the SIKs appeared to be necessary for tumor maintenance, thus indicating that in certain tissues they exert growth-restraining properties. Analysis by using a combination of cellular systems and genetically engineered mouse models have shown that AMPKR kinases SIK1 and SIK3 cooperatively mediate important tumor-suppressor functions of LKB1 in KRAS-driven lung cancer in mice. SIK1 and SIK3, are critical targets in lung cancer. See, e.g., Hollstein et. al., *Cancer Discov.*, 2019, 9:1606-27.

Kinase domain-focused CRISPR screening to human cancer cell lines in search of context-specific dependencies, which revealed a correlation between salt-inducible kinase-3 (SIK3, in a partially redundant manner with SIK2) and Myocyte Enhancer Factor 2C (MEF2C) essentiality in AML. Subsequent mechanistic experiments showed that inactivation of SIK3 induced the formation of HDAC4-MEF2C complexes at distal enhancer elements. This triggered a reduction in vicinal histone lysine acetylation and transcriptional suppression of MEF2C target genes. This study demonstrated a mechanistic link between SIK3 and MEF2C in AML and raised the hypothesis that pharmacological targeting of SIK3 may have therapeutic significance in this disease. See, e.g., Tarumoto et. al., *Blood*, 2020, 135(1):56-70.

Tenalisib (RP6530, 3-(3-fluorophenyl)-2-[(1S)-1-(7H-purin-6-ylamino)propyl]-chromen-4-one), a potent and selective inhibitor with nanomolar potency against the 6 and 7 isoforms of PI3K, is currently being investigated in human clinical trials.

Further reference is made herein to International Publication Nos. WO 14/195888, WO 11/055215 and WO 12/151525 and U.S. Publication Nos. 2014/0364447, 2011/0118257 and 2012/0289496, each of which is incorporated herein by reference in its entirety.

There remains an unmet need for new SIK3 inhibitors for the treatment of diseases and disorders associated with SIK3-mediated events.

SUMMARY OF THE INVENTION

The present invention relates to inhibitors of salt-inducible kinase 3 (SIK3). The SI3K inhibitor compounds described herein are suitable for use, e.g., in a pharmaceutical composition, for the treatment of an SIK3 associated disease, disorder or condition, e.g., a proliferative disease such as cancer. Inhibition of SIK3 kinase may provide beneficial effects in the treatment of certain other diseases and disorders, as described herein.

In one embodiment, the present invention relates to selective SIK3 inhibitors including the following compounds, pharmaceutically acceptable salts thereof, and prodrugs thereof:

(RS)-3-(3-fluorophenyl)-2-(1-((8-hydroxy-9H-purin-6-yl)amino)propyl)-4H-chromen-4-one (Compound M), (S)-3-(3-fluorophenyl)-2-(1-((8-hydroxy-9H-purin-6-yl)amino)propyl)-4H-chromen-4-one (Compound M1), and (R)-3-(3-fluorophenyl)-2-(1-((8-hydroxy-9H-purin-6-yl)amino)propyl)-4H-chromen-4-one (Compound M2).

The chemical structures of Compounds M, M1 and M2 are shown below.

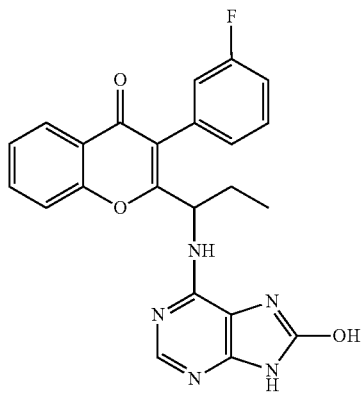

(M)

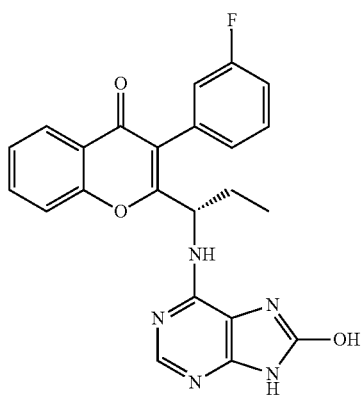

(M1)

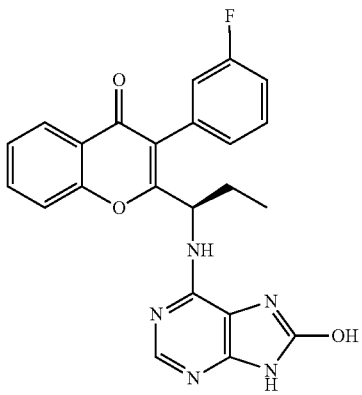

(M2)

Pharmacokinetic evaluation of patient plasma samples from a human clinical trial indicated that tenalisib underwent metabolism to produce in some subjects (S)-3-(3-fluorophenyl)-2-(1-((8-hydroxy-9H-purin-6-yl)amino)propyl)-4H-chromen-4-one (Compound M1). The present inventors have independently synthesized Compound M1 and have surprisingly found it to be inactive against the δ and γ isoforms of PI3K; however, Compound M1 was unexpectedly found to exhibit activity against a different kinase, namely salt-inducible kinase 3 (SIK3).

In one embodiment, any of the compounds described herein (such as Compounds M, M1, and/or M2) are in isolated form. In another embodiment, any of the compounds described herein are isolated in purified form. In yet another embodiment, any of the compounds described herein are in isolated and purified form. In yet another embodiment, any of the compounds described herein are synthesized and are not derived or obtained from a natural source.

In one embodiment, the present invention relates to the compound (S)-3-(3-fluorophenyl)-2-(1-((8-hydroxy-9H-purin-6-yl)amino)propyl)-4H-chromen-4-one (Compound M1), or a pharmaceutically acceptable salt thereof. Another embodiment is a pharmaceutically acceptable salt of (S)-3-(3-fluorophenyl)-2-(1-((8-hydroxy-9H-purin-6-yl)amino)propyl)-4H-chromen-4-one.

In one embodiment, the compound (S)-3-(3-fluorophenyl)-2-(1-((8-hydroxy-9H-purin-6-yl)amino)propyl)-4H-chromen-4-one, or a pharmaceutically acceptable salt thereof, is free or substantially free (e.g., contains less than about 10%, such as less than about 5%, less than about 2.5%, less than about 1%, less than about 0.1% by weight) of (R)-3-(3-fluorophenyl)-2-(1-((8-hydroxy-9H-purin-6-yl)amino)propyl)-4H-chromen-4-one and pharmaceutically acceptable salts thereof.

In another embodiment, the compound (S)-3-(3-fluorophenyl)-2-(1-((8-hydroxy-9H-purin-6-yl)amino)propyl)-4H-chromen-4-one, or a pharmaceutically acceptable salt thereof, has an enantiomeric excess of greater than about 80%, such as greater than about 85%, greater than about 90%, greater than about 95%, greater than about 96%, greater than about 97%, greater than about 98%, greater than about 99%, greater than about 99.5%, greater than about 99.9%, or greater than about 99.99%.

In one preferred embodiment, the present invention relates to (S)-3-(3-fluorophenyl)-2-(1-((8-hydroxy-9H-purin-6-yl)amino)propyl)-4H-chromen-4-one (Compound M1).

In another embodiment, the present invention relates to (R)-3-(3-fluorophenyl)-2-(1-((8-hydroxy-9H-purin-6-yl)amino)propyl)-4H-chromen-4-one (Compound M2) and pharmaceutically acceptable salts thereof. In one embodiment, Compound M2 is (i) free or substantially free (e.g., contains less than about 10%, such as less than about 5%, less than about 2.5%, less than about 1%, less than about 0.1% by weight) of (S)-3-(3-fluorophenyl)-2-(1-((8-hydroxy-9H-purin-6-yl)amino)propyl)-4H-chromen-4-one and pharmaceutically acceptable salts thereof, or (ii) has an enantiomeric excess of greater than about 80%, such as greater than about 85%, greater than about 90%, greater than about 95%, greater than about 96%, greater than about 97%, greater than about 98%, greater than about 99%, greater than about 99.5%, greater than about 99.9%, or greater than about 99.99%.

In yet another embodiment, the present invention relates to (RS)-3-(3-fluorophenyl)-2-(1-((8-hydroxy-9H-purin-6-yl)amino)propyl)-4H-chromen-4-one (Compound M) and pharmaceutically acceptable salts thereof.

In one embodiment, a compound of the present invention is administered as a front-line therapy or as a relapsed-refractory therapy to a patient (preferably a human patient) in need thereof. In another embodiment, a selective SIK3 inhibitor (e.g., Compound M1, or a pharmaceutically acceptable salt thereof) is administered as a front-line therapy or as a relapsed-refractory therapy to a patient (preferably a human patient) in need thereof.

Another embodiment is a method of treating a subject (preferably a human subject) comprising administering to the subject an effective amount of a selective SIK3 inhibitor compound of the present invention. In a preferred embodiment, the selective SIK3 inhibitor compound is Compound M1 or a pharmaceutically acceptable salt thereof.

Yet another embodiment is a method of inhibiting SIK3 activity in a subject (preferably a human subject) by administering to the subject an effective amount of a selective SIK3 inhibitor of the present invention. In one embodiment, the selective SIK3 inhibitor is Compound M1 or a pharmaceutically acceptable salt thereof.

An object of the present invention relates to the uses described herein for the treatment of a subject, in particular of a human subject.

In another aspect, the present invention relates to the use of a compound of the present invention (e.g., Compound M1 or a pharmaceutically acceptable salt thereof) for the preparation of a medicament for use in the treatment of a SIK3 mediated disease, disorder or condition.

In another aspect, the present invention relates to the use of a compound of the present invention (e.g., Compound M1 or a pharmaceutically acceptable salt thereof) for the preparation of a medicament for the treatment of an SIK3 mediated disease, disorder or condition, where the medicament is administered orally.

In additional embodiments of any of the methods and/or uses described herein, the selective SIK3 inhibitor, such as Compound M1 or a pharmaceutically acceptable salt thereof, can be administered to a subject by the oral route, the intravenous route, the intramuscular route, or the intraperitoneal route. In one preferred embodiment, the selective SIK3 inhibitor is administered orally.

In one embodiment, the selective SIK3 inhibitor, such as Compound M1 or a pharmaceutically acceptable salt thereof, is administered as a front-line therapy for the treatment of an SIK3 mediated disease, disorder or condition.

In another embodiment, the selective SIK3 inhibitor, such as Compound M1 or a pharmaceutically acceptable salt thereof, is administered as a relapsed-refractory therapy for the treatment of an SIK3 mediated disease, disorder or condition.

In another aspect, the present invention further provides a pharmaceutical composition comprising one or more compounds of the present invention (such as compound M1 or a pharmaceutically acceptable salt thereof) together with a pharmaceutically acceptable carrier. The pharmaceutical composition may further comprise one or more of additional active agents (such as anti-cancer agents and the active agents discussed below). In one embodiment, the pharmaceutical composition includes a therapeutically effective amount of one or more compounds of the present invention.

Another embodiment is a method of inhibiting SIK3 in a patient (e.g., a patient in need thereof) by administering to the patient an effective amount of at least one compound of the present invention.

Yet another embodiment is a method of treating, preventing, and/or inhibiting a SIK3 kinase mediated disease, disorder or condition (such as cancer or other proliferative disease or disorder) in a patient (e.g., a patient in need thereof) by administering to the patient an effective amount of at least one compound of the present invention.

Yet another embodiment is a method for inhibiting SIK, in particular SIK3 kinase, in a patient (e.g., a patient in need thereof) by administering to the patient an effective amount of at least one compound of the present invention.

Yet another embodiment is a method for treating an inflammatory, autoimmune or proliferative disease via modulation of a protein kinase (such as salt-inducible kinase, e.g., SIK3) by administering to a patient (e.g., a patient in need thereof) an effective amount of at least one compound of the present invention. In one embodiment, the compound of the present invention inhibits SIK3 kinase.

Yet another embodiment is a method for treating an inflammatory, autoimmune or proliferative disease via modulation of a protein kinase (such as salt-inducible kinase, e.g., SIK3) by administering to a patient (e.g., a patient in need thereof) an effective amount of at least one compound of the present invention, in combination (simultaneously or sequentially) with at least one other anti-inflammatory, immunomodulator or anti-cancer agent (or any combination thereof). In one embodiment, the compound of the present invention inhibits SIK3 kinase.

The compounds of the present invention are useful in the treatment of a variety of cancers, including, but not limited to:

carcinoma, including, but not limited to, that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including, but not limited to, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including, but not limited to, acute and chronic myelogenous leukemias, myelodysplastic syndrome and promyelocytic leukemia;

tumors of mesenchymal origin, including, but not limited to, fibrosarcoma and rhabdomyosarcoma;

tumors of the central and peripheral nervous system, including, but not limited to, astrocytoma, neuroblastoma, glioma and schwannomas; and other tumors, including, but not limited to, melanoma, seminoma, teratocarcinoma, osteosarcoma, xenoderoma pigmentosum, keratoctanthoma, thyroid follicular cancer and Kaposi's sarcoma.

In one embodiment, the compounds of the present invention are administered to treat leukemia, such as acute lymphocytic leukemia, acute lymphoblastic leukemia, B-cell lymphoma, T-cell lymphoma, Hodgkin's lymphoma, non-Hodgkins lymphoma, hairy cell lymphoma, Burkett's lymphoma, acute and chronic myelogenous leukemias, myelodysplastic syndrome or promyelocytic leukemia.

Due to the key role of protein kinases in the regulation of cellular proliferation in general, the protein kinase inhibitors of the present invention may act as reversible cytostatic agents, and may be useful therefore in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including but not limited to those types mentioned herein), viral infections (including, but not limited to, herpevirus, poxvirus, Epstein-Barr virus, Sindbis virus and adenovirus), autoimmune diseases (including, but not limited, to systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including, but not limited to, chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain. The compounds of the present invention are also useful in the prevention, inhibition, or suppression of AIDS development in HIV-infected individuals.

The compounds of the present invention can also modulate the level of cellular RNA and DNA synthesis. The compounds of the present invention are therefore useful in the treatment of viral infections, including, but not limited to, HIV, human papilloma virus, herpesvirus, poxvirus, Epstein-Barr virus, Sindbis virus and adenovirus.

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds of the present invention are also useful in inhibiting tumor angiogenesis and metastasis. One embodiment of the present invention is a method of inhibiting tumor angiogenesis or metastasis in a patient (e.g., a patient in need thereof) by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease (COPD), rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder in a patient. The method includes administering an effective amount of one or more compounds of the present invention to the patient.

Examples of immune disorders include, but are not limited to, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are useful as immunosuppressants to prevent transplant graft rejections, allogeneic or xenogeneic transplantation rejection (organ, bone marrow, stem cells, other cells and tissues), and graft—versus—host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft—versus—host disease by administering to a patient in need thereof an effective amount of one or more compounds of the present invention.

The compounds of the present invention are also useful in combination (administered together or sequentially) with known anti-cancer treatments, such as radiation therapy or with cytostatic or cytotoxic or anticancer agents, such as, for example, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators, and any combination of any of the foregoing.

The compounds of the present invention are also useful in combination (administered together or sequentially) with one or more steroidal anti-inflammatory drugs, non-steroidal anti-inflammatory drugs (NSAIDs), immune selective anti-inflammatory derivatives (ImSAIDs), and any combination of any of the foregoing.

The present invention further provides a pharmaceutical composition comprising one or more compounds of the present invention and a pharmaceutically acceptable carrier. The pharmaceutical composition may further comprise one or more additional active ingredients identified herein, such as one or more additional anti-cancer agents.

Yet another embodiment is a method of treating leukemia or lymphoma in a patient in need thereof by administering to the patient a therapeutically effective amount of a compound of the present invention. For example, the compounds of the present invention are effective for treating leukemias and lymphomas selected from, but not limited to, chronic lymphocytic leukemia (CLL), non-Hodgkin lymphoma (NHL), Hodgkin lymphoma (HL), acute myeloid leukemia (AML), multiple myeloma (MM), small lymphocytic lymphoma (SLL), and indolent non-Hodgkin's lymphoma (I-NHL), acute lymphocytic leukemia (ALL), mantle cell lymphoma (MCL), follicular lymphoma, Waldestrom's macroglobulinemia (WM), T-cell lymphoma, B-cell lymphoma, and diffuse large B-cell lymphoma (DLBCL).

Yet another embodiment is a method of treating an autoimmune disorder in a patient in need thereof by administering a therapeutically effective amount of a compound of the present invention. For example, the compounds of the present invention are effective for treating autoimmune disorders such as, but not limited to, asthma, chronic obstructive pulmonary disease (COPD), rheumatoid arthritis, psoriasis, lupus and experimental autoimmune encephalomyelitis (EAE).

Yet another embodiment is a method of treating allergic rhinitis in a patient in need thereof by administering to the patient a therapeutically effective amount of a compound of the present invention.

Yet another embodiment is a pharmaceutical composition for treating a SIK3 mediated disease, disorder or condition comprising a selective SIK3 inhibitor described herein (such as Compound M1 or a pharmaceutically acceptable salt thereof), and, optionally, one or more pharmaceutically acceptable carriers or excipients.

In one embodiment, the pharmaceutical composition further comprises one or more cytostatic, cytotoxic or anticancer agents, or any combination of any of the foregoing.

In one embodiment, the pharmaceutical composition described herein is useful in combination with one or more anti-cancer treatments, one or more cytostatic, cytotoxic or anticancer agents, targeted therapy, or any combination or any of the foregoing. The selective SIK3 inhibitor may be used together or sequentially with one or more anti-cancer treatments one or more cytostatic, cytotoxic or anticancer agents, targeted therapy, or any combination or any of the foregoing.

In one preferred embodiment, the pharmaceutical composition containing the selective SIK3 inhibitor (preferably Compound M1) is suitable for oral administration.

In another embodiment, a compound of the present invention (such as Compound M1 or a pharmaceutically acceptable salt thereof) is administered at a dose of about 25 to about 2000 mg, such as a dose of about 25 to about 1600 mg, about 25 to about 1200 mg, about 25 to about 800 mg, about 25 to about 600 mg, or about 25 to about 400 mg.

In yet another embodiment, a compound of the present invention (such as Compound M1 or a pharmaceutically acceptable salt thereof) is administered at a dose of about 50 to about 2000 mg, such as a dose of about 50 to about 1600 mg, about 50 to about 1200 mg, about 50 to about 800 mg, about 50 to about 600 mg, or about 50 to about 400 mg.

In another embodiment, a compound of the present invention (such as Compound M1 or a pharmaceutically acceptable salt thereof) is administered at a dose of about 200 to about 2000 mg, such as a dose of about 200 to about 1600 mg, about 200 to about 1200 mg, about 200 to about 800 mg, about 200 to about 600 mg, or about 200 to about 400 mg.

In another embodiment, a compound of the present invention (such as Compound M1 or a pharmaceutically acceptable salt thereof) is administered at a dose of about 400 to about 2000 mg, such as a dose of about 400 to about 1600 mg, about 400 to about 1200 mg, about 400 to about 800 mg, or about 400 to about 600 mg.

In another embodiment, a compound of the present invention (such as Compound M1 or a pharmaceutically acceptable salt thereof) is administered at a dose of about 25 to about 2000 mg per day, such as a dose of about 50 to about 1200 mg per day, a dose of about 400 to about 800 mg per day, or a dose of about 200 to about 400 mg per day. In one embodiment, these daily doses are for oral administration of a compound of the present invention (such as Compound M1 or a pharmaceutically acceptable salt thereof).

In certain embodiments, any of the doses described herein may be administered once or twice daily.

A compound of the present invention (such as Compound M1 or a pharmaceutically acceptable salt) thereof may be administered as a single dose or in divided doses.

In another embodiment, a compound of the present invention (such as Compound M1, or a pharmaceutically acceptable salt thereof) is administered once daily. In yet another embodiment, a compound of the present invention (such as Compound M1 or a pharmaceutically acceptable salt thereof) is administered twice daily.

In any of the uses and/or methods described herein, the patient can be a human suffering from relapsed SIK3 mediated disease, disorder or condition.

µM Compound M1, 1 µM azacytidine, or a combination of 5 µM Compound M1 and 1 µM azacytidine.

Figure 4:
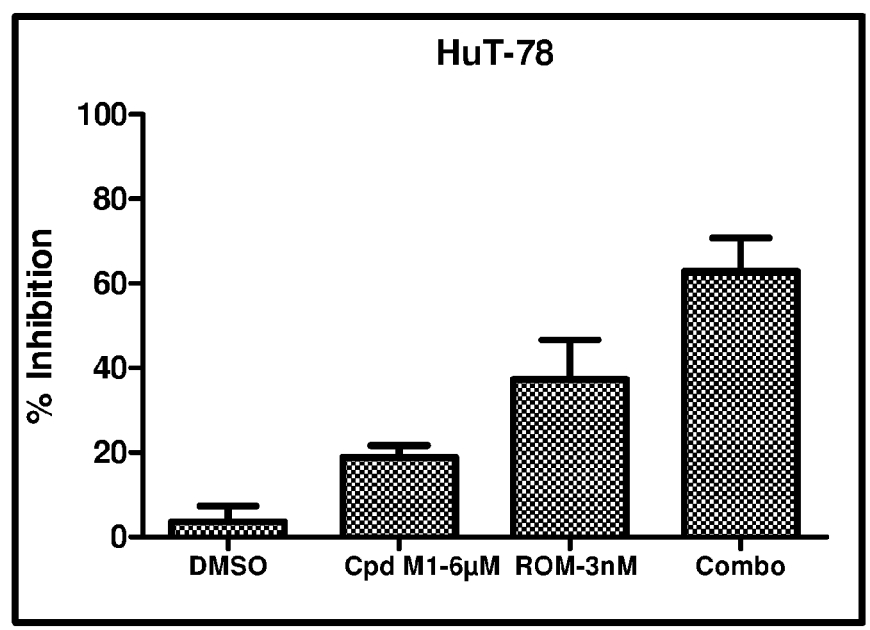

FIG. 4 is a bar graph showing the percentage cell growth inhibition of HuT-78 cell lines by following treatment 6 µM Compound M1, 3 nM romidepsin, or a combination of 6 µM Compound M1 and 3 nM romidepsin.

Figure 5A:
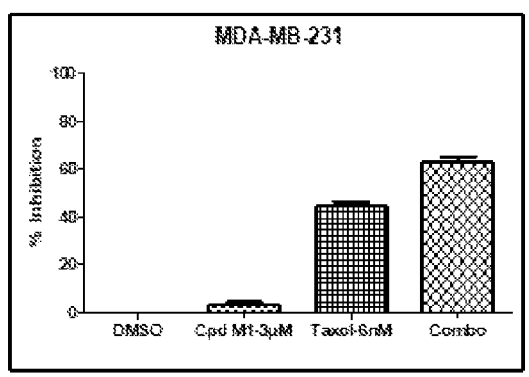

FIG. 5A is a bar graph showing percentage cell growth inhibition of MDA-MB-231 cell lines following treatment with 3 µM Compound M1, 6 nM taxol, or a combination of 3 µM Compound M1 and 6 nM taxol.

Figure 5B:
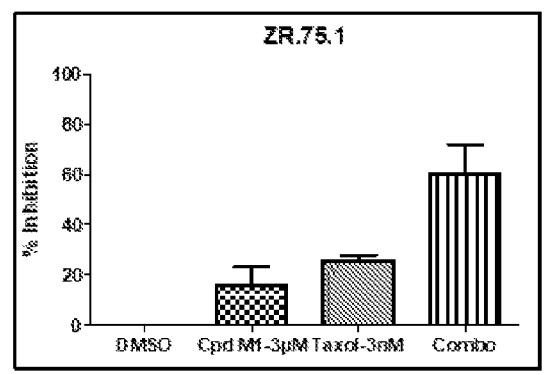

FIG. 5B is a bar graph showing percentage cell growth inhibition of ZR.75.1 cell lines following treatment with 3 µM Compound M1, 3 nM taxol, or a combination of 3 µM Compound M1 and 3 nM taxol.

Figure 5C:
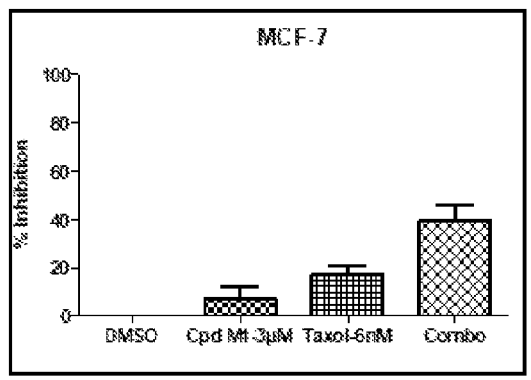

FIG. 5C is a bar graph showing percentage cell growth inhibition of MCF-7 cell lines following treatment with 3 µM Compound M1, 6 nM taxol, or a combination of 3 µM Compound M1 and 6 nM taxol.

Figure 5D:
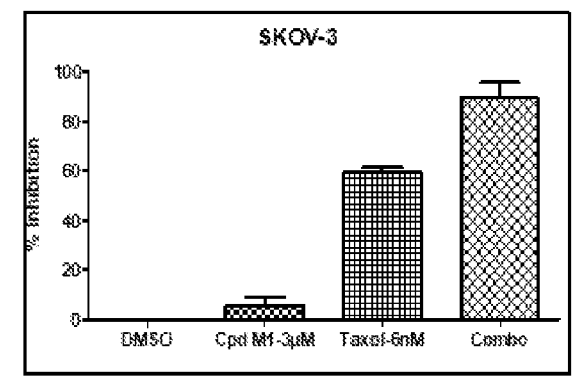

FIG. 5D is a bar graph showing percentage cell growth inhibition of SKOV-3 cell lines following treatment with 3 µM Compound M1, 6 nM taxol, or a combination of 3 µM Compound M1 and 6 nM taxol.

Figure 6A:
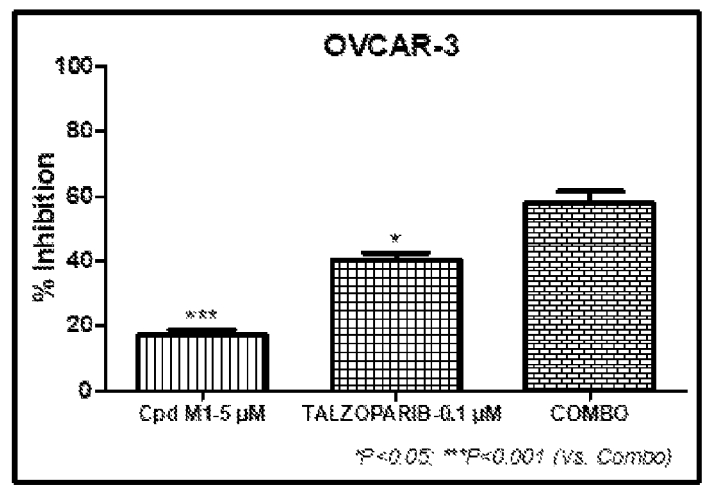

FIG. 6A is a bar graph showing percentage cell growth inhibition of OVCAR-3 cell lines following treatment with 5 µM Compound M1, 0.1 µM talzoparib, or a combination of 5 µM Compound M1 and 0.1 µM talzoparib.

Figure 6B:
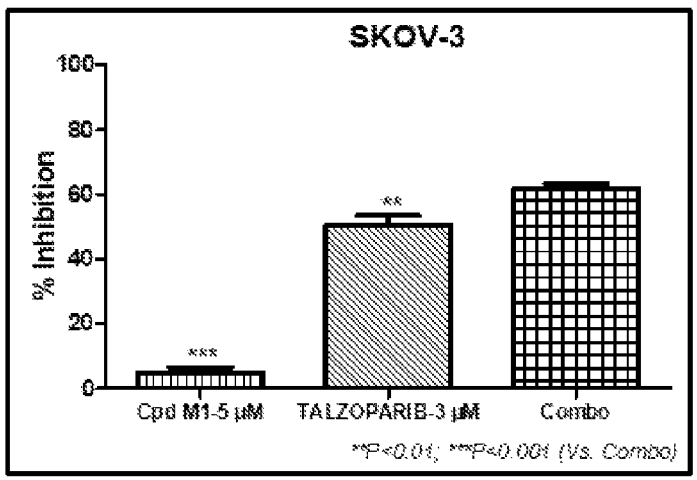

FIG. 6B is a bar graph showing percentage cell growth inhibition of SKOV-3 cell lines following treatment with 5 µM Compound M1, 3 µM talzoparib, or a combination of 5 µM Compound M1 and 3 µM talzoparib.

DETAILED DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

Certain of the compounds described herein may contain one or more asymmetric centers and can thus give rise to enantiomers, diastereomers, and other stereoisomeric forms that can be defined, in terms of absolute stereochemistry, as (R)- or (S)-. Unless otherwise specified, the present chemical entities, pharmaceutical compositions and methods are meant to include all such possible isomers, including racemic mixtures, optically pure forms and intermediate mixtures. For the instance, non-limiting example of intermediate mixtures include a mixture of R:S or S:R isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "prodrug" as used herein refers to a compound which is an inactive precursor of a compound that is converted into its active form in the body by normal metabolic processes. The prodrugs described herein do not include tenalisib. Prodrug design is discussed generally in Hardma, et al. (Eds.), *Goodman and Gilman's The Pharmacological Basis of Therapeutics*, 9th ed., pp. 11-16 (1996). A thorough discussion is provided in Higuchi, et al., *Prodrugs as Novel Delivery Systems*, Vol. 14, ASCD Symposium Series, and in Roche (ed.), *Bioreversible Carriers in Drug Design*, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR' (where R is a drug and R' is a chemical group).

These prodrugs, including esters, are intended to be covered within the scope of this invention.

Additionally, the present invention also includes compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as, for example, tritium ($^3H$), iodine-125 ($^{125}I$) or carbon-14 ($^{14}C$). All isotopic variations of the compounds of the present invention, whether radioactive or not, are encompassed within the scope of the present invention.

"Pharmaceutically acceptable salts" as used herein include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which may be sulphates, nitrates, acetates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range may vary from, for example, between 1% and 15% of the stated number or numerical range.

The term "comprising" (and related terms such as "comprise" or "comprises" or "having" or "including") includes those embodiments, for example, an embodiment of any composition of matter, composition, method, or process, or the like, that "consist of" or "consist essentially of" the described features.

As used herein, and unless otherwise indicated, the term "isolated" means that the compounds described herein are separated from other components of either (a) a natural source, such as a cell or bacterial culture, or (b) a synthetic organic chemical reaction mixture, such as by conventional techniques.

As used herein and unless otherwise indicated, the term "purified" means that when isolated, the isolate contains at least about 90%, such as at least about 95%, at least about 98%, at least about 99% or at least 99.5% of a compound described herein by weight of the isolate.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The terms "co-administration" and "administered in combination with," and their grammatical equivalents, as used herein, encompass administration of two or more agents to a subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including, but not limited to, disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment," "treating," and "ameliorating" are used interchangeably. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compounds and compositions described herein may be administered to a patient at risk of developing a particular disease, or to a patient reporting one or more of the physiological symptoms of a disease, even though a diagnosis of this disease may not have been made.

The term "subject" or "patient" refers to an animal (e.g., a dog, cat, horse, or pig), such as a mammal (for example, a dog, cat, horse, or cow), for example a human. The methods and uses described herein are applicable in both human therapeutics and veterinary applications. In some embodiments, the subject is a mammal. In one preferred embodiment, the subject is a human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP), or high-energy radiation, including, without limitation, x-rays, gamma rays, and neutrons.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents.

"Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia).

"Dermatitis" as used herein refers to any of a large family of diseases of the skin that are characterized by inflammation of the skin attributable to a variety of etiologies.

The methods and uses described herein may be applied to cell populations in vivo or ex vivo (in vitro). "In vivo" means within a living individual, as within an animal or human or in a subject's body. In this context, the methods of the invention may be used therapeutically or prophylactically in an individual. "Ex vivo" or "in vitro" means outside of a living individual. Examples of ex vivo cell populations include, for example, in vitro cell cultures and biological samples including, but not limited to, fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the methods and uses described herein may be used for a variety of purposes, including therapeutic and experimental purposes. For example, the methods and uses described herein may be used ex vivo or in vitro to determine the optimal schedule and/or dosing of administration of a SIK3 selective inhibitor for a given indication, cell type, individual, and other parameters. Information gleaned from such use may be used for experimental or diagnostic purposes or in the clinic to set protocols for in vivo treatment. Other ex vivo uses for which the methods and uses described herein may be suited are described below or will become apparent to those skilled in the art.

In one aspect, the present invention relates to selective SIK-3 inhibitors. Suitable selective SIK3 inhibitors of the present invention include the following compounds, pharmaceutically acceptable salts thereof, and prodrugs thereof:

(RS)-3-(3-fluorophenyl)-2-(1-((8-hydroxy-9H-purin-6-yl) amino)propyl)-4H-chromen-4-one (Compound M),
(S)-3-(3-fluorophenyl)-2-(1-((8-hydroxy-9H-purin-6-yl) amino)propyl)-4H-chromen-4-one (Compound M1), and
(R)-3-(3-fluorophenyl)-2-(1-((8-hydroxy-9H-purin-6-yl) amino)propyl)-4H-chromen-4-one (Compound M2).

Of these three compounds (M, M1 and M2), compound M1 was found to be the most potent SIK-3 inhibitor. Compound M1 exhibits an $IC_{50}$ of 237 nM for SIK3 inhibition when measured using enzymatic radiometric assay. Compound M2 inhibited SIK-3 activity by 100% at a concentration of 1 µM.

When mRNA expression levels of mouse IL-10, TNFα and arginase-1 were measured using real-time PCR, compound M1 was found to be equally potent as dasatinib in mouse IL-10, but more potent than dasatinib for TNFα mRNA expressions. See FIGS. 2A, 2B and 2C.

Furthermore, in THP-1, U937, and MV-4-11, compound M1 showed synergistic activity when combined with azacytidine or ventoclax. See FIGS. 3A-3F. Similarly, synergistic results were obtained when compound M1 was combined with romedepsin (in HuT-78 cell lines), with taxol (MDA-MB-231, MCF-7, ZR.75.1 and SK-OV-3 cell lines) and with talzoparib (OVCAr-3 and SK-OV-3 cell lines). See FIG. 4.

Pharmaceutical Compositions

In one aspect, the present invention provides a pharmaceutical composition comprising one or more compounds of the present invention (e.g., compound M1 or a pharmaceutically acceptable salt thereof) and one or more pharmaceutically acceptable carriers or excipients. In one embodiment, the pharmaceutical composition includes a therapeutically effective amount of a compound of the present invention (e.g., compound M1). The pharmaceutical composition may include one or more additional active ingredients as described herein.

The pharmaceutical carriers and/or excipients may be selected from diluents, fillers, salts, disintegrants, binders, lubricants, glidants, wetting agents, controlled release matrices, colorants, flavorings, buffers, stabilizers, solubilizers, and any combinations of any of the foregoing.

In one embodiment, the pharmaceutical compositions described herein may contain from about 0.1 mg to about 1,000 mg, such as from about 1 mg to about 1,000 mg, from about 20 mg to about 800 mg, from about 50 mg to about 600 mg, from about 50 mg to about 600 mg, or from about 100 mg to about 400 mg of one or more compounds of the present invention (e.g., compound M1).

The pharmaceutical compositions described herein can be administered alone or in combination with one or more other active agents. Where desired, the subject compounds and other agent(s) may be mixed into a preparation or both components may be formulated into separate preparations to use them in combination separately or at the same time.

The compounds and pharmaceutical compositions of the present invention can be administered by any route that enables delivery of the compounds to the site of action, such as orally, intranasally, topically (e.g., transdermally), intraduodenally, parenterally (including intravenously, intraarterially, intramuscularally, intravascularally, intraperitoneally or by injection or infusion), intradermally, by intramammary, intrathecally, intraocularly, retrobulbarly, intrapulmonary (e.g., aerosolized drugs) or subcutaneously (including depot administration for long term release e.g., embedded-under the—splenic capsule, brain, or in the cornea), sublingually, anally, rectally, vaginally, or by surgical implantation (e.g., embedded under the splenic capsule, brain, or in the cornea).

The pharmaceutical compositions described herein can be administered in solid, semi-solid, liquid or gaseous form, or may be in dried powder, such as lyophilized form. The pharmaceutical compositions can be packaged in forms convenient for delivery, including, for example, solid dosage forms, such as capsules, sachets, cachets, gelatins, papers, tablets, suppositories, pellets, pills, troches, and lozenges. The type of packaging will generally depend on the desired route of administration. Implantable sustained release formulations are also contemplated, as are transdermal formulations.

Methods of Treatment

The amount of the compound(s) of the present invention (e.g., compound M1) to be administered is dependent on the mammal being treated, the severity of the disorder or condition, the rate of administration, the disposition of the compound and the discretion of the prescribing physician. However, an effective dosage is in the range of about 0.001 to about 100 mg/kg body weight per day, preferably about 1 to about 35 mg/kg/day, in single or divided doses. For a 70 kg human, this would amount to about 0.05 to about 7 g/day, preferably about 0.05 to about 2.5 g/day An effective amount of a compound of the invention may be administered in either single or multiple doses (e.g., twice or three times a day).

The compounds of the present invention may be used in combination with one or more of anti-cancer agents (e.g., chemotherapeutic agents), therapeutic antibodies, and radiation treatment.

The compounds of the invention may be formulated or administered in conjunction with other agents that act to relieve the symptoms of inflammatory conditions such as encephalomyelitis, asthma, and the other diseases described herein. These agents include, e.g., non-steroidal anti-inflammatory drugs (NSAIDs).

The invention also provides methods of using the compounds or pharmaceutical compositions of the present invention to treat disease conditions, including, but not limited to, diseases associated with malfunctioning of SIK3 kinase.

In one embodiment, the treatment methods provided herein comprise administering to a subject a therapeutically effective amount of a compound of the invention. In one embodiment, the present invention provides a method of treating an inflammation disorder, including autoimmune diseases, in a subject. The method comprises administering to the subject a therapeutically effective amount of a compound of the present invention.

The disorders, diseases, or conditions treatable with a compound or composition provided herein, include, but are not limited to, inflammatory or allergic diseases, including systemic anaphylaxis and hypersensitivity disorders, atopic dermatitis, urticaria, drug allergies, insect sting allergies, food allergies (including celiac disease and the like), anaphylaxis, serum sickness, drug reactions, insect venom allergies, hypersensitivity pneumonitis, angioedema, erythema multiforme, Stevens-Johnson syndrome, atopic keratoconjunctivitis, venereal keratoconjunctivitis, giant papillary conjunctivitis, and mastocytosis;

inflammatory bowel diseases, including Crohn's disease, ulcerative colitis, ileitis, enteritis, and necrotizing enterocolitis;

vasculitis, and Behcet's syndrome;

psoriasis and inflammatory dermatoses, including dermatitis, eczema, allergic contact dermatitis, viral cutaneous pathologies including those derived from human papillomavirus, HIV or RLV infection, bacterial, flugal, and other parasital cutaneous pathologies, and cutaneous lupus erythematosus;

asthma and respiratory allergic diseases, including allergic asthma, exercise induced asthma, allergic rhinitis, otitis media, hypersensitivity lung diseases, chronic obstructive pulmonary disease and other respiratory problems;

autoimmune diseases and inflammatory conditions, including but are not limited to, lupus erythematosus, systemic lupus erythematosus (SLE), multiple sclerosis, polyarthritis, primary biliary cirrhosis, psoriasis, rheumatoid arthritis, psoriatic arthritis, gouty arthritis, spondylitis, reactive arthritis, chronic or acute glomerulonephritis, lupus nephritis, Reiter's syndrome, Takayasu's arteritis, temporal arteritis (also known as "giant cell arteritis"), autoimmune pulmonary inflammation, autoimmune thyroiditis, autoimmune inflammatory eye disease, vitiligo, and vulvodynia. Other disorders include bone-resorption disorders and thrombosis;

cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; and pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity.

In certain embodiments, the cancer or cancers treatable by the methods and/or uses described herein include, but are not limited to, leukemias, including, but not limited to, acute leukemia, acute lymphocytic leukemia, acute myelocytic leukemias such as myeloblasts, promyelocyte, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML);

chronic leukemias, including, but not limited to, chronic myelocytic (granulocytic) leukemia, chronic lymphocytic leukemia, and hairy cell leukemia;

polycythemia vera;

lymphomas, including, but not limited to, Hodgkin's disease and non-Hodgkin's disease;

multiple myelomas, including, but not limited to, smoldering multiple myeloma, nonsecretory myeloma, osteosclerotic myeloma, plasma cell leukemia, solitary plasmacytoma, and extramedullary plasmacytoma;

Waldenstrom's macroglobulinemia;

monoclonal gammopathy of undetermined significance;

benign monoclonal gammopathy;

heavy chain disease;

bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma;

brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma;

breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer;

adrenal cancer, including, but not limited to, pheochromocytom and adrenocortical carcinoma;

thyroid cancer, including, but not limited to, papillary or follicular thyroid cancer, medullary thyroid cancer, and anaplastic thyroid cancer;

pancreatic cancer, including, but not limited to, insulinoma, gastrinoma, glucagonoma, vipoma, somatostatin-secreting tumor, and carcinoid or islet cell tumor;

pituitary cancer, including, but limited to, Cushing's disease, prolactin-secreting tumor, acromegaly, and diabetes insipidus;

eye cancer, including, but not limited, to ocular melanoma such as iris melanoma, choroidal melanoma, and cilliary body melanoma, and retinoblastoma;

vaginal cancer, including, but not limited to, squamous cell carcinoma, adenocarcinoma, and melanoma;

vulvar cancer, including, but not limited to, squamous cell carcinoma, melanoma, adenocarcinoma, basal cell carcinoma, sarcoma, and Paget's disease;

cervical cancers, including, but not limited to, squamous cell carcinoma, and adenocarcinoma;

uterine cancer, including, but not limited to, endometrial carcinoma and uterine sarcoma;
ovarian cancer, including, but not limited to, ovarian epithelial carcinoma, borderline tumor, germ cell tumor, and stromal tumor;
esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma;
stomach cancer, including, but not limited to, adenocarcinoma, fungating (polypoid), ulcerating, superficial spreading, diffusely spreading, malignant lymphoma, liposarcoma, fibrosarcoma, and carcinosarcoma;
colon cancer;
rectal cancer;
liver cancer, including, but not limited to, hepatocellular carcinoma and hepatoblastoma;
gall bladder cancer, including, but not limited to, adenocarcinoma;
cholangiocarcinomas, including, but not limited to, pappillary, nodular, and diffuse;
lung cancer, including, but not limited to, non-small cell lung cancer, squamous cell carcinoma (epidermoid carcinoma), adenocarcinoma, large-cell carcinoma, and small-cell lung cancer;
testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor);
prostate cancer, including, but not limited to, adenocarcinoma, leiomyosarcoma, and rhabdomyosarcoma;
penal cancer;
oral cancer, including, but not limited to, squamous cell carcinoma;
basal cancer;
salivary gland cancer, including, but not limited to, adenocarcinoma, mucoepidermoid carcinoma, and adenoidcystic carcinoma;
pharynx cancer, including, but not limited to, squamous cell cancer and verrucous;
skin cancer, including, but not limited to, basal cell carcinoma, squamous cell carcinoma and melanoma, superficial spreading melanoma, nodular melanoma, lentigo malignant melanoma, and acral lentiginous melanoma;
kidney cancer, including, but not limited to, renal cell cancer, adenocarcinoma,
hypernephroma, fibrosarcoma, and transitional cell cancer (renal pelvis and/or uterer);
Wilms' tumor;
bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas
See, e.g., Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America.

It will be appreciated that the treatment methods and uses described herein are useful in the fields of human medicine and veterinary medicine. Thus, the individual to be treated may be a mammal, preferably a human, or other animal. For veterinary purposes, individuals include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The present invention also relates to a method of treating a hyperproliferative disorder in a subject comprising administering to said mammal a therapeutically effective amount of a compound of the present invention or a pharmaceutically acceptable salt thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

EXAMPLES

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.
Preparation Procedures
Intermediate 1: (S)-2-(1-((9H-purin-6-yl)amino)propyl)-3-(3-fluorophenyl)-4H-chromen-4-one: Preparation procedures for intermediate 1 are disclosed in International Publication No. WO 2014/195888, which is incorporated by reference, as Compound A1.
Intermediate 2: (S)-2-(1-((8-bromo-9H-purin-6-yl)amino)propyl)-3-(3-fluorophenyl)-4H-chromen-4-one: To intermediate 1 (5 g, 12.04 mmol) dissolved in DMF (15 ml), N-Bromo succinimide (3.213 g, 18.054 mmol) was added and stirred at room temperature for 2 hours. The reaction mixture was then added to water slowly (200 mL). The solid precipitated was filtered and washed with water (100 mL), then dried in vacuo to afford 7.0 g of crude compound. The crude product was purified by column chromatography using ethyl acetate and petroleum ether (80:20) as eluent and the product fraction was distilled using a rotavapor to obtain the desired compound (2.3 g) as a pale-yellow solid. Yield: 38.65%. The product was used in the next step without further characterization.
Intermediate 3: (R)-2-(1-((9H-purin-6-yl)amino)propyl)-3-(3-fluorophenyl)-4H-chromen-4-one: Preparation procedures for intermediate 3 are disclosed in International Publication No. WO 14/195888, which is incorporated by reference, as Compound A2.

Intermediate 4: (R)-2-(1-((8-bromo-9H-purin-6-yl)amino)propyl)-3-(3-fluorophenyl)-4H-chromen-4-one: (R)-2-(1-((9H-purin-6-yl)amino)propyl)-3-(3-fluorophenyl)-4H-chromen-4-one (1 g, 2.41 mmol) was dissolved in DMF (3 mL). To this mixture N-Bromo succinimide (0.642 g, 3.61 mmol) was added and the mixture stirred for 6 hours at room temperature. The reaction mixture was then added slowly to water (40 mL). The solid precipitated was filtered then washed with water (30 mL) and dried in vacuo to afford 1.25 g of crude compound. The crude was purified using Teledyne CombiFlash® (HPLC) with methanol and dichloromethane (1.5:98.5) as eluent. The combined pure fractions from CombiFlash were distilled using a rotavapor to obtain the desired compound (0.62 g) as a pale-yellow solid. Yield: 52.10%. The product was used in the next step without further characterization.

Compound M1 (S)-3-(3-fluorophenyl)-2-(1-((8-hydroxy-9H-purin-6-yl)amino)propyl)-4H-chromen-4-one To (S)-2-(1-((8-bromo-9H-purin-6-yl)amino)propyl)-3-(3-fluorophenyl)-4H-chromen-4-one (2.3 g, 4.65 mmol) (Intermediate 2), formic acid (23 mL) was added and the resulting mixture was refluxed at 100° C. for 16 hours. The reaction mixture was then cooled to room temperature and the pH of the reaction mixture was adjusted to ~7 using saturated aqueous sodium bicarbonate solution, and extracted with dichloromethane (2×100 mL). The combined organic layers were washed with water (100 mL), dried over anhydrous sodium sulphate and evaporated to obtain the crude product. The crude product was purified by combi-flash using ethyl acetate and petroleum ether (80:20) as eluent. The combined pure fractions from CombiFlash were distilled using a rotavapor to obtain the desired compound (300 mg) as an off-white solid. Yield: 15%. Melting point: 196-199° C. MS (m/z): 431.5 (M+). 1H-NMR (δppm, DMSO-d6, 400 MHz): 11.32 (s, 1H), 9.90 (s, 1H), 8.03 (d, J 7.4, 1H), 7.92 (s, 1H), 7.82 (t, J 7.4, 1H), 7.62 (d, J 8.2, 1H), 7.52-7.45 (m, 2H), 7.30-7.15 (m, 3H), 6.81 (d, J 7.2, 1H), 4.97 (q, J 7.3, 1H), 2.01-1.80 (m, 2H), 0.87 (t, J 6.7, 3H).

Compound M2 (R)-3-(3-fluorophenyl)-2-(1-((8-hydroxy-9H-purin-6-yl)amino)propyl)-4H-chromen-4-one Formic acid (6 mL) was added to (R)-2-(1-((8-bromo-9H-purin-6-yl)amino)propyl)-3-(3-fluorophenyl)-4H-chromen-4-one (0.60 g, 1.21 mmol) (Intermediate 4). This mixture was refluxed at 100° C. for 16 hours. The reaction mixture was cooled to room temperature and the pH of the reaction mixture adjusted to ~7 using saturated aqueous sodium bicarbonate solution. The aqueous reaction mixture was then extracted with dichloromethane (2×100 mL). The combined organic layers were washed with water (100 mL). The organic layer was dried using anhydrous $Na_2SO_4$ and evaporated to obtain the desired compound as a brown solid (900 mg). The crude product was purified by combi-flash using methanol and dichloromethane (DCM) (2.5:97.5) as eluent. The combined pure fractions from combi-flash were distilled using a rotavapor to obtain a pale brown solid (150 mg). To the solid, diethyl ether (5 mL) was added and stirred for 1 hour at room temperature. Following filtration, the solid was washed with diethyl ether (2 mL) then dried in vacuo for 1 hour to obtain the desired compound (100 mg) as a pale brown solid. Yield: 19%. Melting point: 215-218° C. 1H-NMR (δppm, DMSO-d6, 400 MHz): 11.33 (s, 1H), 9.90 (s, 1H), 8.04 (d, J 7.6, 1H), 7.92 (s, 1H), 7.83 (t, J 7.6, 1H), 7.63 (d, J 8.4, 1H), 7.51-7.45 (m, 2H), 7.25-7.21 (m, 3H), 6.83 (d, J 7.2, 1H), 4.96 (q, J 7.2, 1H), 1.98-1.83 (m, 2H), 0.87 (t, J 7.2, 3H).

Biological Assays

The pharmacological properties of the compounds described herein may be confirmed by a number of pharmacological assays, including those exemplified below.

Example 1

Assay 1: Determination of $IC_{50}$ of Compound M1 Against Human Salt-Inducible Kinase-3 (SIK3) Using an Enzymatic Radiometric Assay Assay Protocol SIK3 (human) was incubated with 8 mM MOPS pH 7.0, 0.2 mM EDTA, 100 uM of the peptide KKKVSRSG-LYRSPSMPENLNRPR (Substrate), 10 mM Mg Acetate and [gamma-33P-ATP] (specific activity and concentration as required) in the presence of Compound M1.

The reaction was initiated by the addition of the Mg/ATP mix.

After incubation for 40 minutes at room temperature, the reaction was stopped by the addition of phosphoric acid to a concentration of 0.5%.

10 μL of the reaction mixture was then spotted onto a P30 filtermat and washed four times for 4 minutes in 0.425% phosphoric acid and once in methanol prior to drying and scintillation counting.

Figure 1:
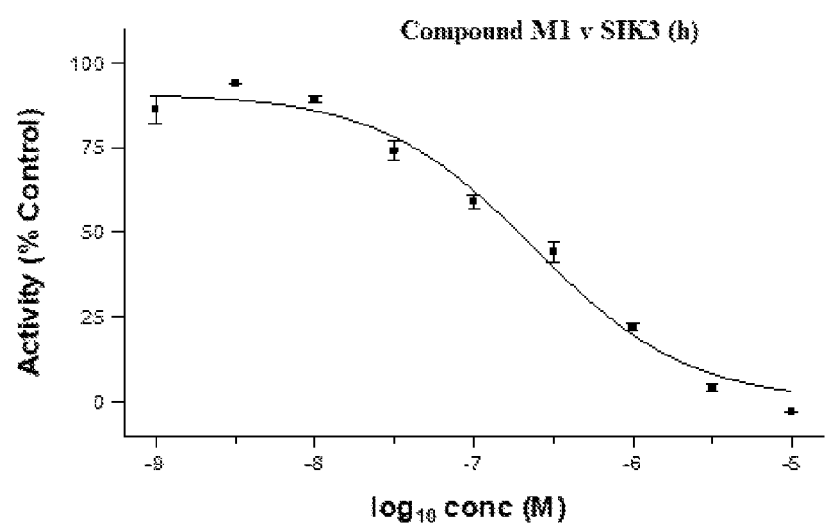
FIG. 1 is a graph showing the SIK3 inhibitory activity of Compound M1 as measured by an enzymatic radiometric assay over various concentrations of Compound M1.

The $IC_{50}$ value was calculated using GraphPad Prism. The results are shown in FIG. 1.

Compound M1 exhibits an $IC_{50}$ of 237 nM for SIK3 inhibition

Example 2

Assay 2: Evaluation of mRNA Expression Levels of IL-10, TNFα, and Arginase-1 in LPS-Stimulated (1 μg/ml) Mouse Bone Marrow Derived Macrophages (BMDM).

Mouse-Bone Marrow Cell Isolation

Femur bones from healthy mice were collected taking all aseptic precautions.

Bones were severed proximal to each joint using sterile scissors.

A 10 ml syringe with 25-G needle was filled with cold sterile wash medium (DMEM/F12 medium+10% FBS (fetal bovine serum)+1% Penicillin-streptomycin).

The needle was inserted into bone marrow cavity of femur and the cavity was flushed with 2-5 mL of wash medium, until the bone cavity appeared white.

Wash medium was collected in a 50 mL tube and centrifuged at 500×g for 10 minutes at room temperature.

Cells were resuspended in DMEM/F12 medium and cell count was taken.

Macrophage Culture $4 \times 10^5$ cells/10 ml in DMEM/F12+10% FBS+1% Penicillin-streptomycin media (Complete Media) were cultured in a flask at 37° C. and 5% $CO_2$ incubator by adding 50 ng/ml mouse Macrophage Colony Stimulating Factor (M-CSF) to the media.

On day 3, another 5 ml of complete medium (with M-CSF) was added to the flask.

On day 7, culture supernatants were removed.

Adherent cells were washed with wash sterile wash medium and medium was discarded.

Cells were gently scraped to dislodge into 5-10 ml of cold DMEM/F12 medium (complete medium).

Cells were then centrifuged at 400×g, 4° C. and the supernatant was discarded.

Cells were resuspended in 3-5 mL of DMEM/F12 medium (complete medium) for plating and counted.

Cells should be essentially 100% macrophages at this time.

Assay Protocol $0.5 \times 10^6$ mouse-bone marrow derived macrophages were plated in 500 μL of DMEM/F12K complete media containing mouse M-CSF (50 ng/ml).

Cells were incubated at 37° C. and 5% $CO_2$ overnight.

Cells were treated with DMSO or COMPOUND M1 for 1 h followed by addition of LPS (1 μg/ml) to polarize the macrophages and control (non-polarized cells) did not receive LPS treatment.

2 hours later, media was removed, and the cells were washed with sterile PBS and RNA was extracted using Tri-Reagent.

cDNA synthesis was carried out using "First Strand cDNA Synthesis Kit" (Thermo Scientific) as per manufacturer's instructions.

Real-Time PCR was done at Invitrogen (Life Technologies, Gurgaon) to measure the mRNA expression levels of mouse IL-10, TNFα and arginase-1.

Results

Figure 2A:
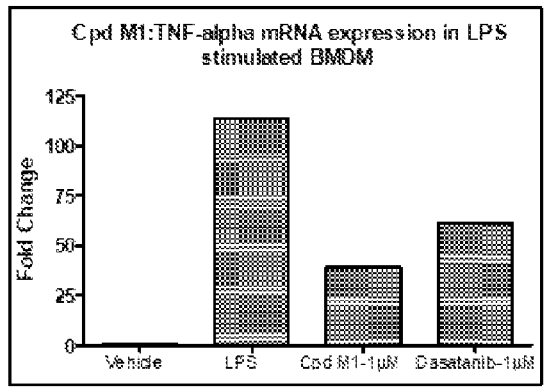
FIG. 2A is a bar graph showing the change in mRNA expression levels of TNFα in LPS stimulated mouse bone marrow derived macrophages (BMDM) after exposure with a control, 1 μM Compound M1, and 1 μM dasatinib.
Figure 2B:
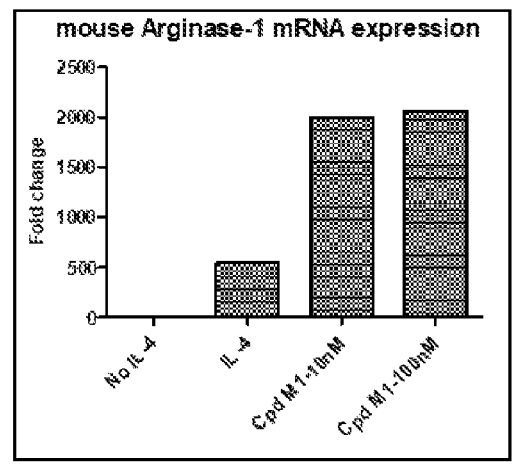
FIG. 2B is a bar graph showing the change in mRNA expression levels of Arginase-1 in LPS stimulated mouse BMDM for various concentrations of Compound M1 (1 μM and 10 μM).
Figure 2C:
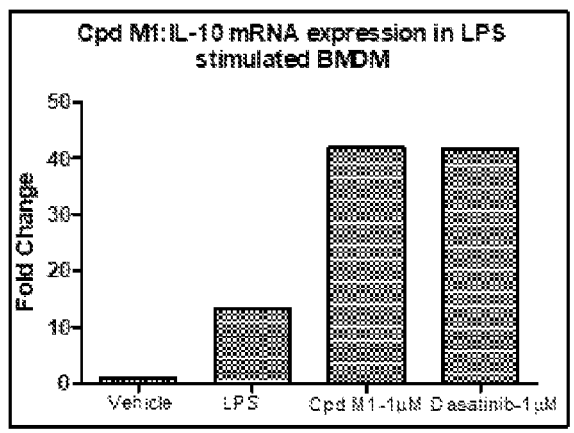
FIG. 2C is a bar graph showing the change in mRNA expression levels of IL-10 in LPS stimulated BMDM for 1 μM Compound M1 and 1 μM dasatinib.
Figure 3A:
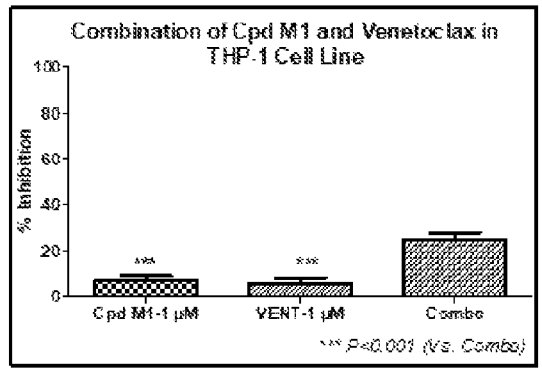
FIG. 3A is a bar graph showing the percentage cell growth inhibition of THP-1 cell lines following treatment with 1 μM Compound M1, 1 μM venetoclax, or a combination of 1 μM Compound M1 and 1 μM venetoclax.
Figure 3B:
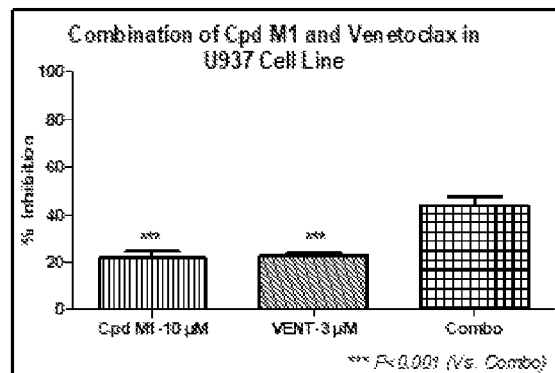
FIG. 3B is a bar graph showing the percentage cell growth inhibition of U937 cell lines following treatment with 10 μM Compound M1, 3 μM venetoclax, or a combination of 10 μM Compound M1 and 3 μM venetoclax.
Figure 3C:
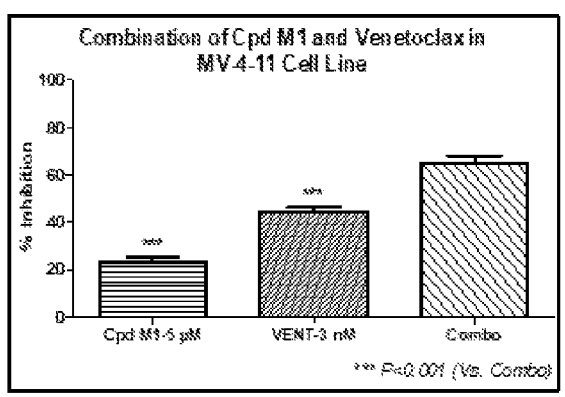
FIG. 3C is a bar graph showing the percentage cell growth inhibition of MV-4-11 cell lines following treatment with 5 μM Compound M1, 3 nM venetoclax, or a combination of 5 μM Compound M1 and 3 nM venetoclax.
Figure 3D:
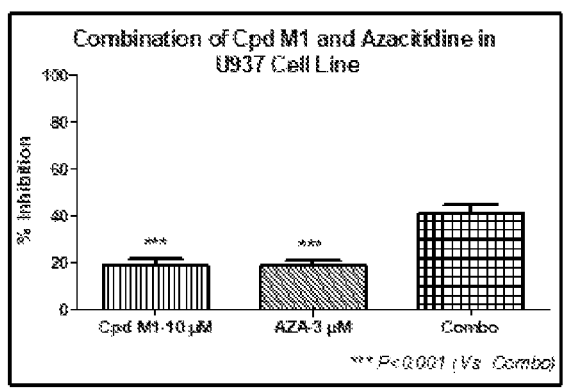
FIG. 3D is a bar graph showing the percentage cell growth inhibition of U937 cell lines following treatment with 10 μM Compound M1, 3 μM azacytidine, or a combination of 10 μM Compound M1 and 3 μM azacytidine.
Figure 3E:
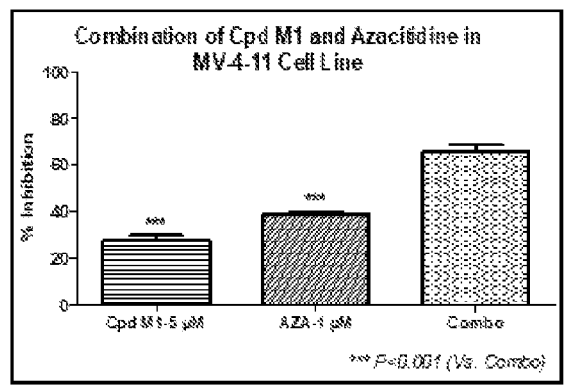
FIG. 3E is a bar graph showing the percentage cell growth inhibition of MV-4-11 cell lines following treatment with 5

Fold change in the mRNA expression was calculated by $2^{-\Delta\Delta Ct}$ method and data was plotted using GraphPad Prism. The results are shown in FIGS. 2A, 2B and 2C.

Example 3

Assay 3: TNFα Levels in LPS-Stimulated (1 μg/ml) Human Macrophages Following Treatment with Compound M1 was Estimated by ELISA.

Isolation of Human PBMCs (Peripheral Blood Mononuclear Cells)

Freshly drawn heparinised blood was diluted with an equal volume of 1×PBS in a 50 ml centrifuge tube and mixed gently.

The diluted blood was added to HiSep (HiSep LSM1077 from Himedia) slowly along the wall of the tube so that the blood does not mix with the HiSep and remains as an overlay (final ratio of blood:1×PBS:HiSep is 1:1:1).

The tube was centrifuged at 400×g for 30 min at 4'C.

After centrifugation, the top plasma phase was discarded. The second layer from the top, the buffy coat, was collected carefully with a serological pipette and placed in a new 50 ml centrifuge tube. The volume was made up to 50 mL with 1×PBS and centrifuged at 250×g for 10 min at room temperature.

The supernatant was discarded and red blood cells (RBCs) were resuspended with 5 mL ACK lysis buffer to facilitate RBC lysis and left at room temperature for 5 min. The tube was filled up with 1×PBS and centrifuged at 250×g for 10 min at room temperature.

The supernatant was discarded and the pellet was re-suspended in 5 mL of RPMI complete media.

Cells were counted on a haemocytometer.

Human Macrophage Differentiation $7 \times 10^6$ cells/well in a 6-well plate in RPMI CM media were plated and incubated at 37° C. for 1-4 hours to facilitate monocyte adherence.

Once monocytes have adhered, the supernatant was removed and 2 mL of RPMI containing 50 ng/mL of human M-CSF-1 was added to the monocytes. Human M-CSF-1 was replenished every 4 days.

Differentiation to macrophages occurred between 7-11 days.

Assay Protocol

Cells were scraped and centrifuged at 250×g for 8 mins and cell concentration was determined.

$0.2 \times 10^6$ human macrophages were plated/well in a 96-well plate in RPMI CM with 50 ng/mL of Human M-CSF-1 and incubated overnight at 37° C. and 5% $CO_2$.

Human macrophages were treated with compound M1 for 1 hour followed by addition of LPS (1 μg/mL). The control (non-polarized cells) did not receive LPS treatment.

The supernatant was collected after 4 hours.

TNFα (Ebiosciences catalog No. 88-7346-88) was estimated by ELISA according to manufacturer's instructions.

Absorbance readings were normalized with the control sample readings

Results

Fold change was calculated, and graphs were plotted using GraphPad Prism. TNFα cytokine levels measured in LPS stimulated human macrophages supernatants were reduced by 75% following treatment with compound M1.

Example 4

Assay 4: Compound M1 as a Single Agent or in Combination with Azacytidine, or Venetoclax was Determined in the AML Lines: THP-1, U937, and MV-4-11.

The table below shows the information and conditions for each cell type.

| Cell Line | Growth Media | No. of Cells | Incubation Time after Treatment (hrs) |
|---|---|---|---|
| THP-1 | RPMI + 10% FBS + 1% Pen-Strep | 10000 | 72 |
| U937 | RPMI + 10% FBS + 1% Pen-Strep | 10000 | 72 |
| MV-4-11 | IMDM + 10% FBS + 1% Pen-Strep | 5000 | 72 |

Day 0

The cells were pelleted and counted.

Cells were plated at desired density (100 μl/well) in complete media in a 96-well plate in triplicates. A column for Day "0" reading was also seeded (18-20 hrs after initial plating and before addition of the inhibitors)

Plates were incubated at 37° C. and 5% $CO_2$.

Day 1

10 μl of MTT (5 mg/ml) were added to the column designated for Day "0". It was mixed well and incubated at 37° C. and 5% $CO_2$ for 3.5 h. Cells were pelleted down at 4000 rpm for 10 minutes.

Media was aspirated out and 150 µl of DMSO were added to the cells and mixed by pipetting to dissolve the crystals Plate was read at $A_{560\ nm}$ and $A_{640\ nm}$.

Day 2

A series of dilutions of the inhibitors were initially made in 100% DMSO and further diluted in growth medium.

Cells were treated with either single agent of DMSO, compound M1, azacytidine or venetoclax, a combination of compound M1 and azacytidine, or a combination of compound M1 and venetoclax. DMSO concentration in the well was 0.2%.

Plates were incubated at 37° C. and 5% $CO_2$

Day 5

15 µl of 5 mg/mL (final concentration of 1×) of MTT were added to the test wells and mixed well.

Plates were incubated at 37° C. and 5% $CO_2$ for 3.5 hours

After incubation, cells are pelleted down at 4000 rpm for 10 minutes. Media was aspirated and 150 µl of DMSO per well were added. Crystals were dissolved by repeated pipetting.

The plate was read at $A_{560\ nm}$ and $A_{640\ nm}$.

Results

Reference absorbance values were subtracted from test absorbance values. Day 0 values were subtracted from final day absorbance values for determining cell growth. Percent cell growth inhibitions were calculated. The results are shown in FIGS. 3A, 3B, 3C, 3D and 3E.

Example 5

Assay 5: Combination of Compound M1 with Standard Agents in HuT-78 Cell Lines

The table below shows the information and conditions for each cell type.

| Cell Line | Growth Media | No. of Cells | Incubation Time After Treatment (hrs) |
|---|---|---|---|
| HuT-78 | IMDM + 20% FBS + 1% Pen-Strep | 20000 | 72 |

Day 0

The HuT-78 cells were pelleted and counted.

Cells were plated at desired density (100 µl/well) in complete media in a 96-well plate in triplicates. A column for Day "0" reading was also seeded. (18-20 hrs after initial plating and before addition of the inhibitors)

Plates were incubated at 37° C. and 5% $CO_2$.

Day 1

10 µl of MTT (5 mg/ml) were added to the column designated for Day "0". It was mixed well and incubated at 37° C. and 5% $CO_2$ for 3.5 hours. Cells were pelleted down at 4000 rpm for 10 minutes.

Media was aspirated out and 150 µl of DMSO were added to the cells and mixed by pipetting to dissolve the crystals The plate was read at $A_{560\ nm}$ and $A_{640\ nm}$.

Day 2

A series of dilutions of the inhibitors were initially made in 100% DMSO and further diluted in growth medium.

Cells were treated with either single agent of DMSO, compound M1, romidepsin, or a combination of compound M1 and romidepsin (HuT-78). DMSO concentration in the well was 0.2%.

Plates were incubated at 37° C. and 5% $CO_2$ for 72 hours.

Day 5

15 µl of 5 mg/ml (final concentration of 1×) of MTT were added to the test wells and mixed well.

Plates were incubated at 37° C. and 5% $CO_2$ for 3.5 hours.

After incubation, cells are pelleted down at 4000 rpm for 10 min. Media was aspirated and 150 µl of DMSO per well were added. Crystals were dissolved by repeated pipetting.

The plate was read at $A_{560\ nm}$ and $A_{640\ nm}$.

Results

Reference absorbance values were subtracted from test absorbance values. Day 0 values were subtracted from final day absorbance values for determining cell growth. % Cell growth inhibitions were calculated. The results are shown in FIG. 4.

Example 5A

Assay 6: Combination of Compound M1 with Standard Agents in Different Cell Lines The table below shows the information and conditions for each cell type.

| Cell Line | Growth Media | No. of Cells | Incubation Time After Treatment (hrs) |
|---|---|---|---|
| MDA-MB-231 | RPMI + 10% FBS + 1% Pen-Strep | 1500 | 72 |
| ZR.75.1 | RPMI + 10% FBS + 1% Pen-Strep | 2000 | 72 |
| MCF-7 | MEM + 10% FBS + 1% Pen-Strep | 1500 | 72 |
| SK-OV-3 | McCoy's + 10% FBS + 1% Pen-Strep | 2500 | 72 |

Day 0

The cells were pelleted and counted.

Cells were plated at desired density (100 µl/well) in complete media in a 96-well plate in triplicates. A column for Day "0" reading was also seeded. (18-20 hrs after initial plating and before addition of the inhibitors)

Plates were incubated at 37° C. and 5% $CO_2$.

Day 1

10 µl of MTT (5 mg/ml) were added to the column designated for Day "0". It was mixed well and incubated at 37° C. and 5% $CO_2$ for 3.5 h. Cells were pelleted down at 4000 rpm for 10 minutes.

Media was aspirated out and 150 µl of DMSO were added to the cells and mixed by pipetting to dissolve the crystals The plate was read at $A_{560\ nm}$ and $A_{640\ nm}$.

Day 2

A series of dilutions of the inhibitors were initially made in 100% DMSO and further diluted in growth medium.

Cells were treated with either single agent of DMSO, compound M1, taxol, and a combination of compound M1 and taxol (MDA-MB-231, MCF-7, ZR.75.1 and SK-OV-3). DMSO concentration in the well was 0.2%.

The plates were incubated at 37° C. and 5% $CO_2$

Day 5

15 µl of 5 mg/ml (final concentration of 1×) of MTT were added to the test wells and mixed well.

Plates were incubated at 37° C. and 5% $CO_2$ for 3.5 hours

After incubation, cells are pelleted down at 4000 rpm for 10 min. Media was aspirated and 150 µl of DMSO per well were added. Crystals were dissolved by repeated pipetting.

The plate was read at $A_{560\ nm}$ and $A_{640\ nm}$.

Results

Reference absorbance values were subtracted from test absorbance values. Day 0 values were subtracted from final day absorbance values for determining cell growth. % Cell growth inhibitions were calculated. The results are shown in FIGS. 5A, 5B, 5C and 5D.

Example 5B

Assay 5: Combination of Compound M1 with Standard Agents in Different Cell Lines The table below shows the information and conditions for each cell type.

| Cell Line | Growth Media | No. of Cells | Incubation Time after Treatment (hrs) |
|---|---|---|---|
| SK-OV-3 | McCoy's + 10% FBS + 1% Pen-Strep | 2500 | 72 |
| OVCAR-3 | RPMI + 20% FBS + 1% Pen-Strep | 5000 | 72 |

Day 0

The cells were pelleted and counted.

Cells were plated at desired density (100 µl/well) in complete media in a 96-well plate in triplicates. A column for Day "0" reading was also seeded. (18-20 hrs after initial plating and before addition of the inhibitors)

Plates were incubated at 37° C. and 5% $CO_2$.

Day 1

10 µl of MTT (5 mg/ml) were added to the column designated for Day "0". It was mixed well and incubated at 37° C. and 5% $CO_2$ for 3.5 h. Cells were pelleted down at 4000 rpm for 10 minutes.

Media was aspirated out and 150 µl of DMSO were added to the cells and mixed by pipetting to dissolve the crystals The plate was read at $A_{560\ nm}$ and $A_{640\ nm}$.

Day 2

A series of dilutions of the inhibitors were initially made in 100% DMSO and further diluted in growth medium.

Cells were treated with either single agent of DMSO, compound M1, talzoparib, and combination of compound M1 and talzoparib (OVCAr-3 and SK-OV-3). DMSO concentration in the well was 0.2%.

The plates were incubated at 37° C. and 5% $CO_2$

Day 5

15 µl of 5 mg/ml (final concentration of 1×) of MTT were added to the test wells and mixed well.

Plates were incubated at 37° C. and 5% $CO_2$ for 3.5 hours

After incubation, cells are pelleted down at 4000 rpm for 10 min. Media was aspirated and 150 µl of DMSO per well were added. Crystals were dissolved by repeated pipetting.

The plate was read at $A_{560\ nm}$ and $A_{640\ nm}$.

Results

Reference absorbance values were subtracted from test absorbance values. Day 0 values were subtracted from final day absorbance values for determining cell growth. % Cell growth inhibitions were calculated. The results are shown in FIGS. 6A and 6B.

All publications and patent and/or patent applications cited in this application are herein incorporated by reference to the same extent as if each individual publication or patent application was specifically and individually indicated to be incorporated herein by reference.

What is claimed is:

1. A method of inhibiting a catalytic activity of salt-inducible kinase-3 (SIK3) present in a breast cancer or ovarian cancer cell, comprising contacting the cell with an effective amount of 3-(3-fluorophenyl)-2-(1-((8-hydroxy-9H-purin-6-yl)amino) propyl)-4H-chromen-4-one or a pharmaceutically acceptable salt thereof.

2. The method of claim 1, wherein the inhibition takes place in a subject suffering from breast cancer.

3. A method for the treatment of breast cancer or ovarian cancer comprising administering to a subject in need thereof an effective amount of 3-(3-fluorophenyl)-2-(1-((8-hydroxy-9H-purin-6-yl)amino) propyl)-4H-chromen-4-one or a pharmaceutically acceptable salt thereof.

4. The method of claim 3, further comprising the step of administering simultaneously or sequentially to the subject at least one other anti-cancer agent.

5. The method of claim 3, wherein the patient suffers from breast cancer.

6. The method of claim 3, wherein the patient suffers from ovarian cancer.

* * * * *